(12) United States Patent
Park et al.

(10) Patent No.: US 9,518,012 B2
(45) Date of Patent: Dec. 13, 2016

(54) METHOD OF PREPARING CORE-SHELL COPPER NANOPARTICLES IMMOBILIZED ON ACTIVATED CARBON AND METHOD OF PREPARING CHALCOGENIDE COMPOUND USING NANOPARTICLES AS CATALYST

(71) Applicant: Pusan National University Industry-University Cooperation Foundation, Busan (KR)

(72) Inventors: Kang Hyun Park, Busan (KR); Sung Kyun Park, Busan (KR); Bu Hyun Youn, Busan (KR); Jin Kyoon Park, Busan (KR); Jung Sub Lee, Busan (KR); Balaji Mohan, Busan (KR); Seong Wan Jang, Busan (KR); Sang Geun Lee, Busan (KR); Cho Hye Yoon, Busan (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 14/862,632

(22) Filed: Sep. 23, 2015

(65) Prior Publication Data
US 2016/0311768 A1    Oct. 27, 2016

(30) Foreign Application Priority Data

Apr. 21, 2015 (KR) .......................... 10-2015-0056043

(51) Int. Cl.
| | | |
|---|---|---|
| *C07C 391/00* | (2006.01) | |
| *C07C 395/00* | (2006.01) | |
| *B01J 23/00* | (2006.01) | |
| *B01J 37/00* | (2006.01) | |
| *C07C 391/02* | (2006.01) | |
| *B01J 23/72* | (2006.01) | |
| *B01J 35/00* | (2006.01) | |
| *B01J 37/16* | (2006.01) | |
| *B01J 37/34* | (2006.01) | |

(52) U.S. Cl.
CPC .............. *C07C 391/02* (2013.01); *B01J 23/72* (2013.01); *B01J 35/0013* (2013.01); *B01J 37/16* (2013.01); *B01J 37/343* (2013.01); *C07C 395/00* (2013.01)

(58) Field of Classification Search
CPC ....... C07C 391/02; C07C 395/00; B01J 23/72; B01J 37/16; B01J 37/343

USPC .......................................... 562/899; 502/345
See application file for complete search history.

(56) References Cited

PUBLICATIONS

Mohan et al. Copper Nanoparticles Catalyzed Se (Te)—Se (Te) Bond Activation: A Straightforward Route Towards Unsymmetrical Organochalcogenides from Boronic Acids. Chem. Cat. Chem. Communications, 2015, vol. 7, pp. 405-412.*
Narayanaperumal et al., "Transition Metal Oxide Nanopowder and Ionic Liquid: an Efficient System for the Synthesis of Diorganyl Selenides, Selenocysteine and Derivatives", J. Braz. Chem. Soc. ,vol. 21, No. 11, pp. 2079-2087, 2010.
Sheno et al., "Synthesis of Different Copper Oxide Nano-Structures From Direct Thermal Decomposition of Porous Copper(II) Metal-Organic Framework Precursors", Int. J. Nanosci. Nanotechnol., vol. 8, No. 2, pp. 99-104, Jun. 2012.
Chaudhuri et al., "Core/Shell Nanoparticles: Classes, Properties, Synthesis Mechanisms, Characterization, and Applications", Chemical Reviews, pp. 2373-2433, 2012.
Wang et al., "A Simple Copper Salt-Catalyzed Synthesis of Unsymmetrical Diaryl Selenides and Tellurides from Arylboronic Acids with Diphenyl Diselenide and Ditelluride", Letter, vol. 13, pp. 2007-2010, 2005.
Nobukazu Taniguchi, "Convenient Synthesis of Unsymmetrical Organochalcogenides Using Organoboronic Acids with Dichalcogenides via Cleavage of the S—S, Se—Se, or Te—Te Bond by a Copper Catalyst", J. Org. Chem., vol. 72, pp. 1241-1245, 2007.
Alves et al., "CuO nanoparticles: an efficient and recyclable catalyst for cross-coupling reactions of organic diselenides with aryl boronic acids", Tetrahedron Letters, vol. 50, pp. 6635-6638, 2009.
Kumar et al., "A convenient and efficient copper-catalyzed synthesis of unsymmetrical and symmetrical diaryl chalcogenides from arylboronic acids in ethanol at room temperature", Tetrahedron, vol. 70, pp. 1763-1772, 2014.

\* cited by examiner

*Primary Examiner* — Sikarl Witherspoon
(74) *Attorney, Agent, or Firm* — Hamre, Schumann, Mueller & Larson, P.C.

(57) ABSTRACT

Disclosed herein is a method of preparing a Cu/Cu$_2$O core-shell copper nanoparticle catalyst having high catalytic activity from [Cu$_3$(BTC)$_2$] and NaBH$_4$ via a simple chemical reduction method. Also disclosed is a method of preparing a chalcogenide compound by using the nanoparticle catalyst as a heterogeneous catalyst in a cross-coupling reaction between a chalcogenide precursor compound and a boron-containing compound. The disclosed cross-coupling reaction is performed via a simple process, and the disclosed nanoparticle catalyst is compatible with various substrates under mild reaction conditions and exhibits excellent recyclability without a reduction in catalytic activity.

17 Claims, 14 Drawing Sheets

METHOD OF PREPARING CORE-SHELL COPPER NANOPARTICLES IMMOBILIZED ON ACTIVATED CARBON AND METHOD OF PREPARING CHALCOGENIDE COMPOUND USING NANOPARTICLES AS CATALYST

BACKGROUND

1. Technical Field

Embodiments of the present invention relate to a method of preparing an immobilized core-shell copper nanoparticle catalyst which can be used as a catalyst in a cross-coupling reaction between a chalcogenide precursor compound and a boron-containing compound, thereby achieving high yield and selectivity, and which is cost-effective because it can be recovered and recycled, and to a cross-coupling reaction between a chalcogenide precursor compound and a boron-containing compound, which is performed using the copper nanoparticle catalyst.

2. Description of the Related Art

Over the past few years, metal nanoparticles have been used in various fields including medicines, materials, environment, energy, etc. Unlike conventional bulky metal materials, these metal nanoparticles have exhibited high reactivity with various molecules due to their large surface areas. In various industrial chemistry fields, the cost effectiveness and environmental friendliness of metal nanocatalysts have become important, and thus it has become important to recycle highly toxic catalysts. In connection with this, many documents have reported the immobilization of metal nanoparticles on various supports, such as charcoal, alumina, porous silica materials, etc. Such metal nanoparticles immobilized on solid supports can be easily recycled and have high reactivity and dispersibility.

Meanwhile, many studies on materials with carbon-selenium bonds have been conducted due to their antimicrobial activity, anticancer activity and antioxidant activity. In addition, a selenium-based ionic liquid is an effective catalyst in the carbonylation of aniline, the oxidation of thiol, and the synthesis of thioacetals and octahydroacridines. For the past few years, studies on new methods for the synthesis of organochalcogens based on $sp^3$, $sp^2$ and sp carbon atoms and selenium or tellurium have been conducted. For the synthesis of these chalcogenides, many methods have been reported, and as an example, methods that use diphenyl diselenide or diphenyl ditelluride as a precursor have been used due to their air stability, environmental friendliness, and industrial applicability. Diphenyl diselenide can react with aryl halides or organic boronic acid to synthesize organochalcogen derivatives. Herein, organic boronic acid and its esters are stable and less toxic, and thus can be industrially used together with various reactants. For this reason, a coupling reaction between diphenyl diselenide and organic boronic acid is useful in the synthesis of asymmetric organochalcogen compounds.

Meanwhile, the use of inexpensive and toxic copper catalysts in catalytic reactions is not preferable in terms of cost effectiveness and efficiency. In recent years, some documents have reported synthesizing aryl selenides using copper salts in the presence of ligands and other additives under the conditions of long reaction time, high temperature and high catalyst loading.

As an example, a document reported the synthesis of diaryl selenide and telluride from aryl boronic acid in the presence of CuI as a catalyst. A representative study thereon was disclosed in L. Wang, M. Wang, and F. Huang, *Synlett* 2005, 13, 2007-2010. In addition, methods that use CuI and bipyridyl ligand to synthesize various asymmetric organochalcogen compounds were reported. A representative study thereon was disclosed in N. Taniguchi, *J. Org. Chem.* 2007, 72, 1241-1245. Furthermore, the cross-coupling reaction of diaryl diselenide, which uses glycerol as an environmentally friendly solvent and CuI as a catalyst, was reported. A representative study thereon was disclosed in D. Alves, C. G. Santos, M. W. Paixao, L. C. Soares, D. Souza, O. E. D. Rodrigues, and A. L. Braga, *Tetrahedron Lett.* 2009, 50, 6635-6638. In addition, the synthesis of diphenyl chalcogenide using a copper salt as a catalyst in the presence of a base, a ligand and a reducing agent was also reported. A representative study thereon was disclosed in A. Kumar, and S. Kumar, *Tetrahedron* 2014, 70, 1763-1772.

The methods using metal salts as disclosed in the above-described prior art documents are performed under homogeneous conditions, and thus have difficulty in the recovery and recycle of catalysts. This increases the synthesis cost and limits the applicability of the reaction. Therefore, there has been a need to develop a catalyst system which is applicable to various functional groups and which does not require a base, a reducing agent or other additives.

SUMMARY

At least one embodiment of the present invention is directed to the provision of a method of preparing a $Cu/Cu_2O$ core-shell copper nanoparticle catalyst which enables a chalcogenide compound to be produced with high yield and selectivity and which is cost-effective because it can be recovered and recycled.

At least one embodiment of the present invention is directed to the provision of a cross-coupling reaction between a chalcogenide precursor compound and a boron-containing compound, which is performed using as a catalyst the Cu/CuzO core-shell nanoparticle catalyst prepared by the above method.

In accordance with an aspect of the present invention, there is provided a method of preparing immobilized copper nanoparticles, the method comprising:

adding $Cu(NO_3)_2 \cdot 2.5H_2O$ and $H_3BTC$ to an organic solvent, followed by stirring to prepare a mixture;

separating a solid product from the mixture, and drying the product in a vacuum to yield $[Cu_3(BTC)_2]$;

adding an aqueous solution of $NaBH_4$ dropwise to an aqueous solution of the $[Cu_3(BTC)_2]$ in water to obtain reduced copper particles;

adding the reduced copper particles to a mixture of ethyl alcohol and activated carbon, followed by sonication at room temperature and refluxing to obtain a solution of copper nanoparticles imnmobilized on the activated carbon; and cooling the solution of the copper nanoparticles imobilized on the activated carbon, and purifying a product resulting from the cooling of the solution.

In accordance with another aspect of the present invention, there is provided a method of preparing a chalcogenide compound via a cross-coupling reaction between diphenyl dichalcogenide and phenylboronic acid, wherein the method is performed in the presence of the above-described immobilized copper nanoparticle catalyst.

In accordance with still another aspect of the present invention, there is provided a method of preparing a chalcogenide compound via a cross-coupling reaction between dibenzyl dichalcogenide and phenylboronic acid, wherein the method is performed in the presence of the above-described immobilized copper nanoparticle catalyst.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
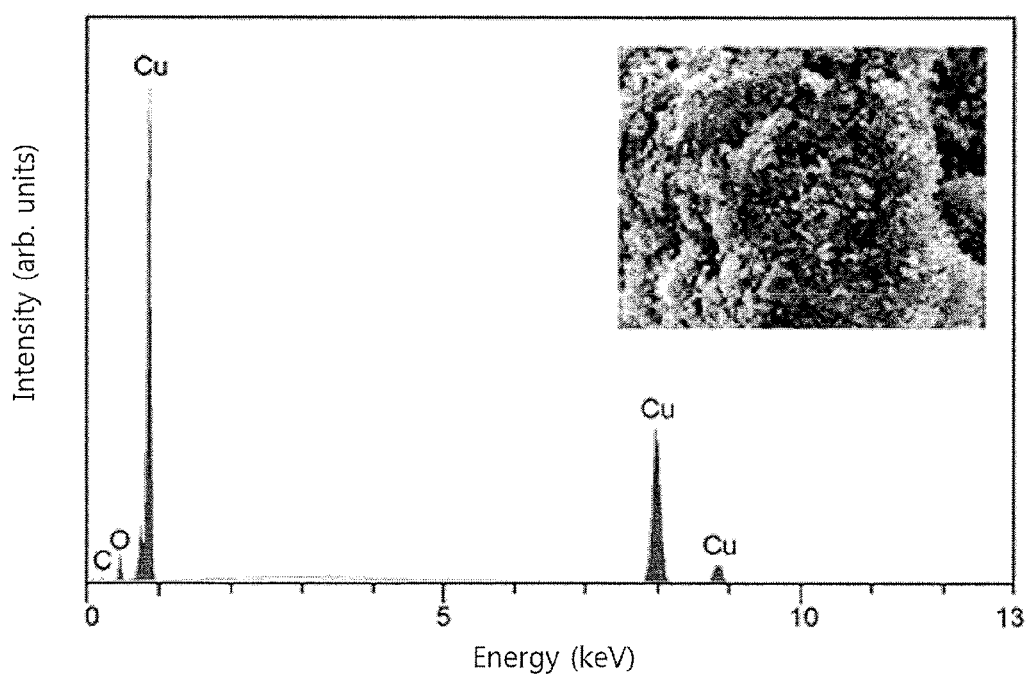
FIG. 1 is a graph showing the results of the EDS analysis of copper nanoparticles according to an embodiment of the present invention.

A copper nanoparticle catalyst according to the present invention is prepared from $[Cu_3(BTC)_2]$ synthesized via a hydrothermal method.

The copper nanoparticles prepared as described above exhibits high reactivity and excellent recyclability in the synthesis of organochalcogen derivatives.

In the present invention, all compounds were obtained from Aldrich Chemical Co. and TCI Chemical Co. and used without purification. Solvents were obtained from Daejung Co., Ltd. and Samchun Chemical Co., Ltd. and used without purification.

The mass spectra of products were measured by Pusan National University using a mass spectrometer (Shimadzu GCMS-QP 2010 Ultra). The morphology of products was characterized by the National NanoFab Center using transmission electron microscopy (TEM) (FEI, Tecnai F30 Super-Twin) by placing a few drops of the corresponding colloidal solution on a carbon-coated copper grid (200 meshes, F/C coated, Ted Pella Inc., Redding, Calif., USA). Scanning electron microscope (SEM) images were taken using VEGA3 TESCAN equipment. Elemental compositions were obtained using energy-dispersive X-ray spectroscopy (EDS) (550i, IXRF Systems, Inc.), and X-ray diffraction (XRD) patterns were recorded by Pusan National University using a Pigaku GDX-11P3A diffractomneter. Nitrogen-adsorption isotherms were measured using Tristar II 3020 V1.03 equipment at $-196°$ C. Inductively coupled plasma atomic emission spectroscopy (ICP-OES) was performed using a Thermo Scientific iCap 6300 ICP spectrometer.

The present invention will be described in detail with reference to specific examples below. However, it is to be understood that these examples are only for illustrative purposes and are not intended to limit the scope of the present invention.

A general method of preparing a copper nanoparticle catalyst having a $Cu/Cu_2O$ core-shell structure according to the present invention is as follows:

Preparation Example 1

Synthesis of $[Cu_3(BTC)_2]$ $[Cu_3(BTC)_2]$ particles were synthesized via a solvothermal method. More specifically, $Cu(NO_3)_2 \cdot 2.5H_2O$ (10 g, 43 mmol) and $H_3BTC$ (BTC=benzene-1,3,5-tricarboxylate) (5 g, 23 mnol) were added to a mixed solvent of $DMF/EtOH/H_2O$ (250 mL, 1:1:1) and stirred for 10 minutes. The mixture was allowed to react at $85°$ C. for 20 hours, after which it was cooled at room temperature and centrifuged at 10,000 rpm for 20 minutes.

Thereafter, the solid product was separated by decanting the mother liquor, after which it was washed with DI and then washed with dichlorcimethane three times within 3 days. The product was dried under a high vacuum to yield $[Cu_3(BTC)_2]$ as blue crystals.

Example 1

Preparation of Copper Nanoparticles Immobilized on Activated Carbon

The $[Cu_3(BTC)_2]$ prepared in Preparation Example 1 was reduced via a chemical reduction method and used as a precursor for preparing copper nanoparticles. More specifically, a solution of $NaBH_4$ (0.312 g, 82.66 mnol) in a water solvent (5 mL) was added dropwise to a solution of $[Cu_3(BTC)\pm](0.5$ g, 0.8266 mmnol) in a water solvent (20 mL) while the mixture solution was being stirred for 10 minutes, thereby reducing the $[Cu_3(BTC)_2]$. Thereafter, the mixture solution was further stirred for 30 minutes, followed by centrifugation at 10,000 rpm for 20 minutes.

The mother liquid was decanted, and the remaining black solid precipitate was washed with a large amount of deionized water and washed with ethanol. The washed precipitate was dried under a high vacuum to yield reduced copper particles as black powder. The reduced copper particles were added to a mixture of ethyl alcohol and activated carbon, and then sonicated at room temperature for 30 minutes, after which the mixture was allowed to react under reflux for 6 hours under strong magnetic stirring. Thereafter, the reaction solution was centrifuged with ethanol at 10,000 rpm for 20 minutes three times.

Thereafter, copper nanoparticles immobilized on the activated carbon were dried in a vacuum. The content of copper immobilized on the activated carbon was about 33.1% as measured by ICP-OES analysis.

The obtained copper nanoparticles were characterized by energy-dispersive spectrometry (EDS), transmission electron microscopy (TEM), X-ray diffraction (XRD) analysis, X-ray photoelectron spectroscopy (XPS) and $N_2$-adsorption isotherms. To determine the surface area, pore volume and pore size of the copper nanoparticles immobilized on activated carbon, the Brunauer-Emmett-Teller (BET) equation was used.

FIG. 1 is a graph showing the results of the EDS analysis of copper nanoparticles according to an embodiment of the present invention. Referring to FIG. 1, an SEM image is shown as an insert, and EDS measurements indicate that small amounts of oxygen and copper atoms are present in the copper nanoparticles. This indicates that a copper oxide layer is present on the surface of the nanoparticles.

Figure 2A:
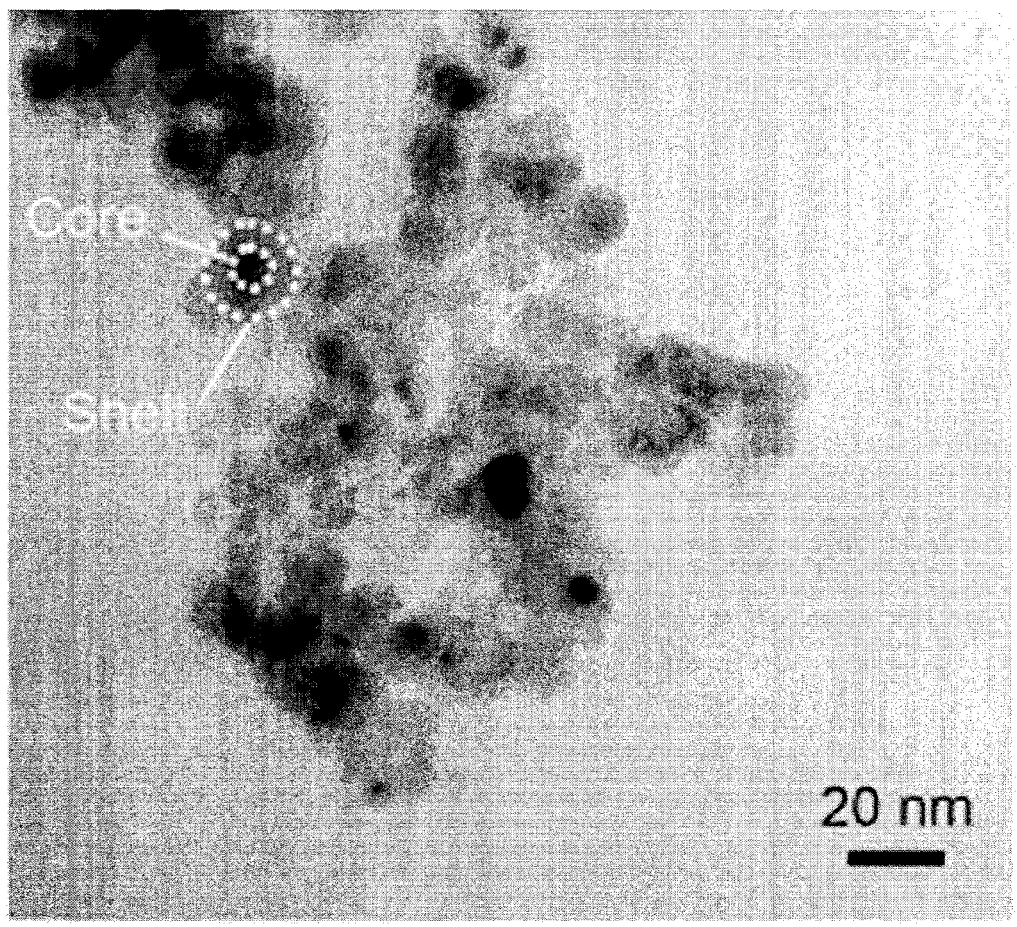
FIG. 2A is an SEM image of core-shell copper nanoparticles coated with $Cu_2O$.
Figure 2B:
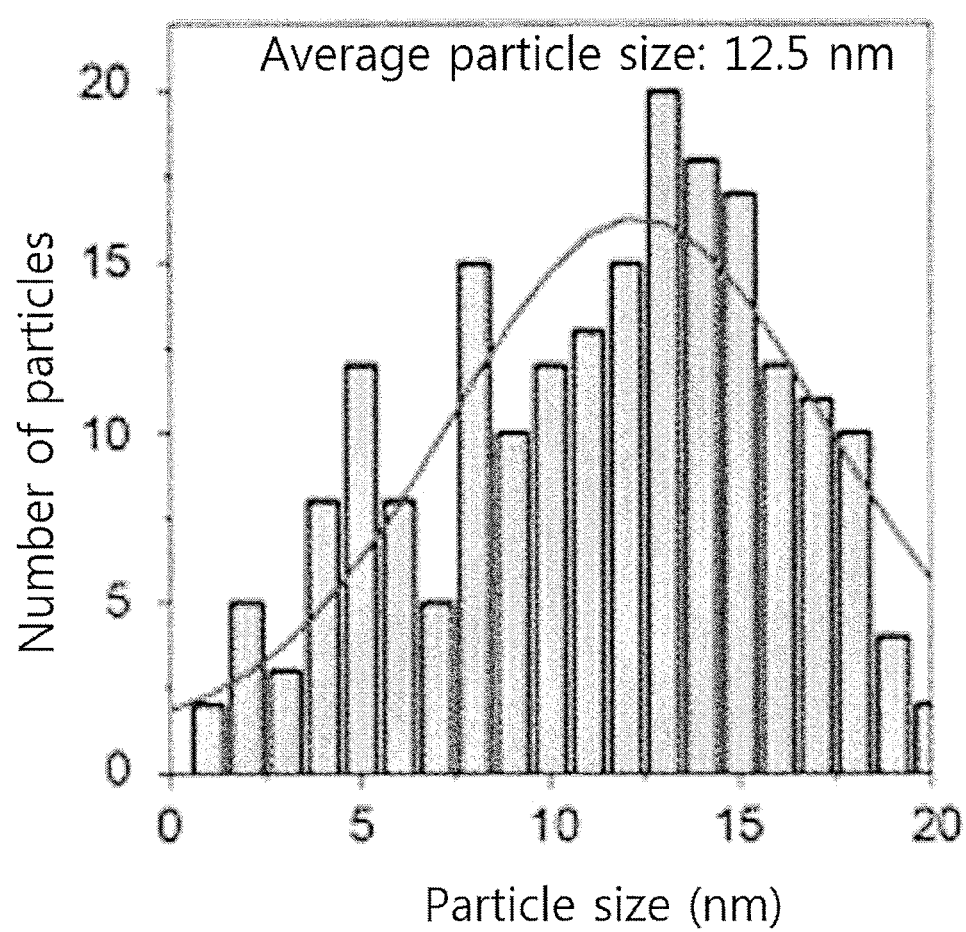
FIG. 2B is a view showing the particle size distribution of copper nanoparticles coated with $Cu_2O$.
Figure 2C:
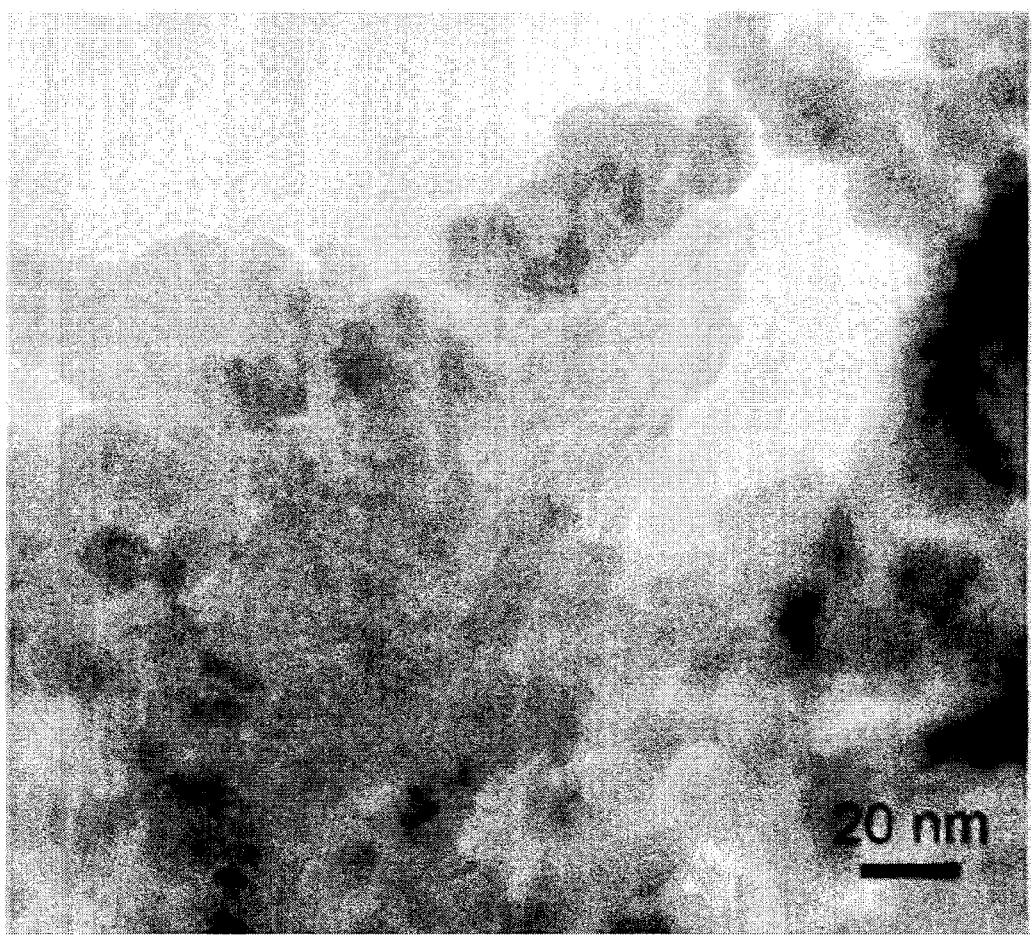
FIG. 2C is a TEM image of copper nanoparticles immobilized on activated carbon.
Figure 2D:
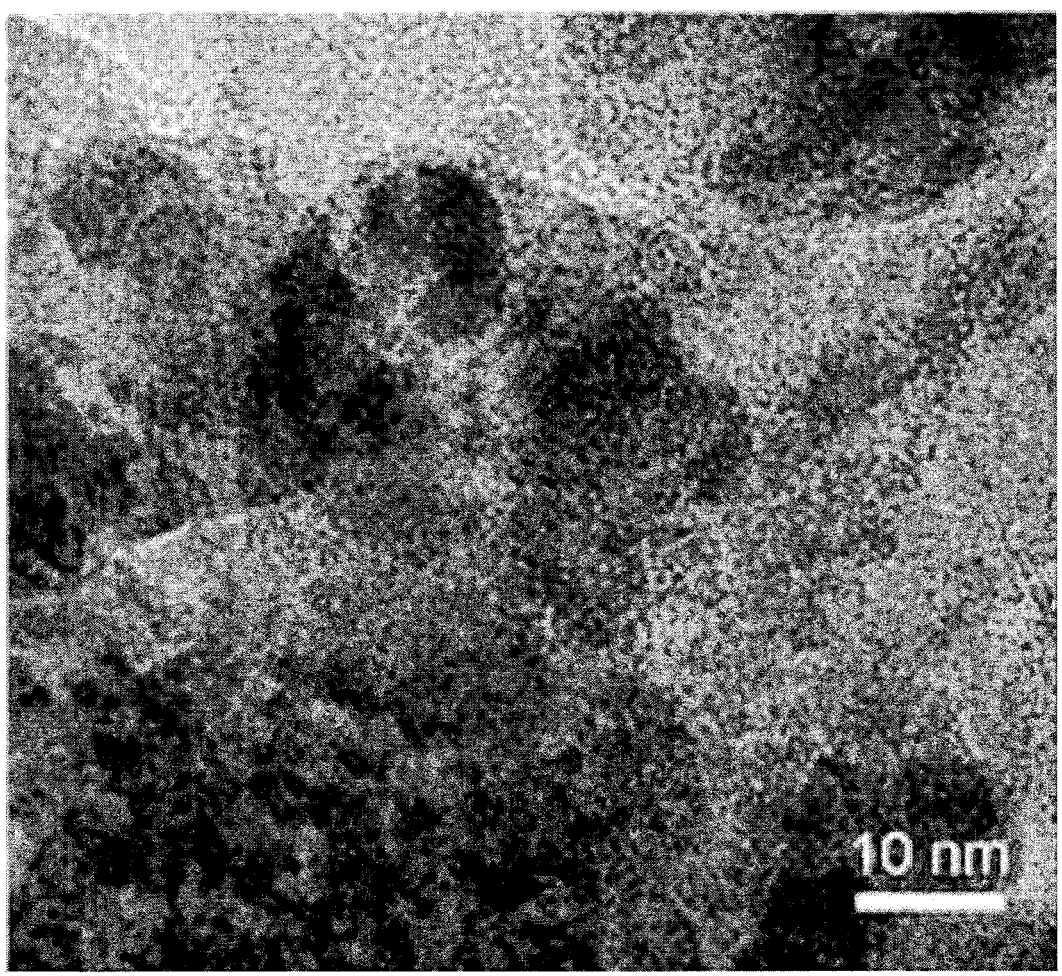
FIG. 2D is a high-resolution TEM image of copper nanoparticles imobilized on activated carbon.

FIG. 2A is an SEM image of core-shell copper nanoparticles coated with $Cu_2O$, FIG. 2B is a view showing the particle size distribution of copper nanoparticles coated with $Cu_2O$, FIG. 2C is a TEM image of copper nanoparticles immobilized on activated carbon, and FIG. 2D is a high-resolution TEM (HRTEM) image of copper nanoparticles immobilized on activated carbon. Referring to FIGS. 2A to 2D, the morphology of the core-shell copper nanoparticles prepared according to the present invention and the immobilization of these nanoparticles on activated carbon can be seen. Furthermore, the TEM image indicates that the surface of the copper nanoparticles was coated with $Cu_2O$ by oxidation in air. As shown in FIG. 2A, such particles had a regular polygonal shape and were mostly monodispersed, and some of these particles had a Cu core and a $Cu_2O$ shell formed by oxidation of the copper nanoparticles. Referring to FIG. 2B, the TEM topography indicates that the particle size was about 12.5 nm; and referring to FIG. 2C, it can be seen that the copper nanoparticles were immobilized on activated carbon. Referring to FIG. 2D, the high-resolution TEM image of the copper nanoparticles immobilized on activated carbon indicates that the nanoparticles were well dispersed on activated carbon.

Figure 3A:
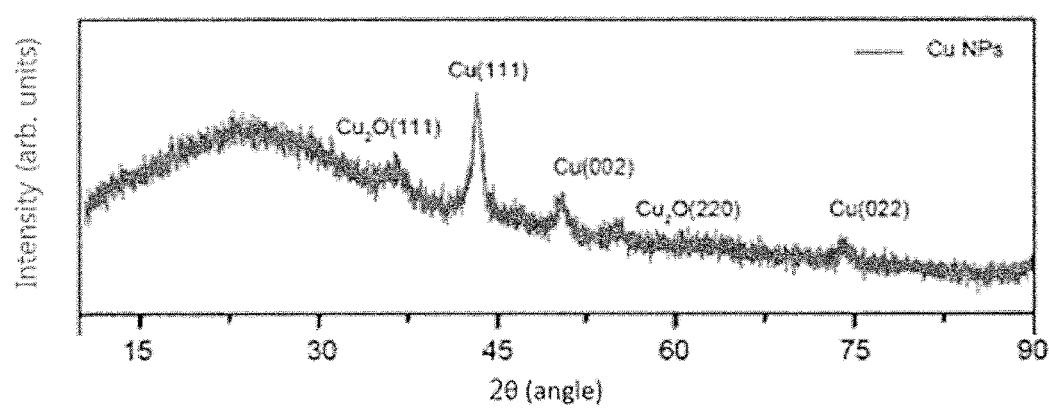
FIG. 3A shows the X-ray diffraction (XRD) pattern of copper nanoparticles according to an embodiment of the present invention.

FIG. 3A shows the X-ray diffraction (XRD) pattern of copper nanoparticles synthesized from $[Cu_3(BTC)_2]$ according to an embodiment of the present invention. The powder XRD pattern of the copper nanoparticles indicates the presence of metal copper. Referring to FIG. 3A, the XRD analysis indicates that the core portion of the prepared copper nanoparticles is composed of zero-valent copper and the shell portion is composed of monovalent copper. The average particle size (D) of the nanoparticles was calculated from the X-ray diffraction data using the following Scherrer's formula: D=0.9 k/(B cos θB), where k is the X-ray wavelength (Cu-$K_\alpha$=1.5406 Å) used in the experiment, B is the full-width at half-maximum of a particular peak (in radians), and B is the peak position. For the (111) peak, it can be seen that the grain size normal to the scattering plane is approximately 9.6 nm. The X-ray diffraction pattern shown in FIG. 3A indicates that the $Cu_2O$ shell was formed by the oxidation of the copper core in air.

Figure 3B:
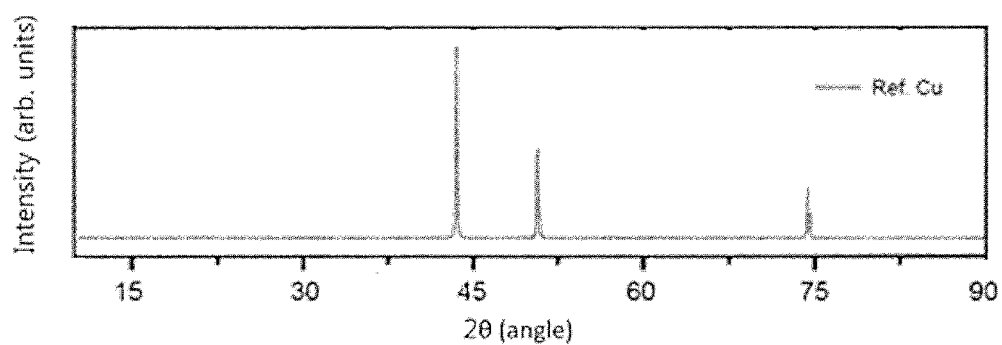
FIG. 3B shows the X-ray diffraction pattern of conventional bulky copper.
Figure 3C:
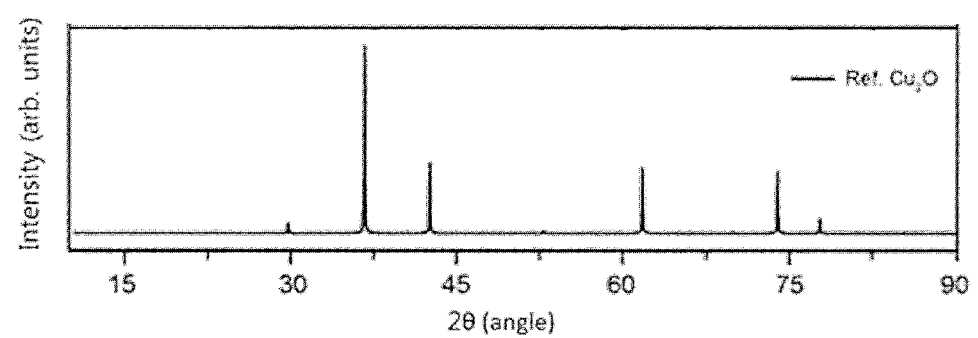
FIG. 3C shows the X-ray diffraction pattern of conventional $Cu_2O$.

Referring to FIG. 3A, the three main peaks at q=43.2, 50.3 and 74.18° correspond to the (111), (002) and (022) planes of the copper phase (JCPDS No. 04-0836), and small peaks correspond to the (111) and (220) planes in the $Cu_2O$ phase. FIG. 3B shows the X-ray diffraction pattern of conventional bulky copper for comparison, and FIG. 3C shows the X-ray diffraction pattern of conventional $Cu_2O$ (JCPDS No. 77-0199) for comparison.

Figure 4:
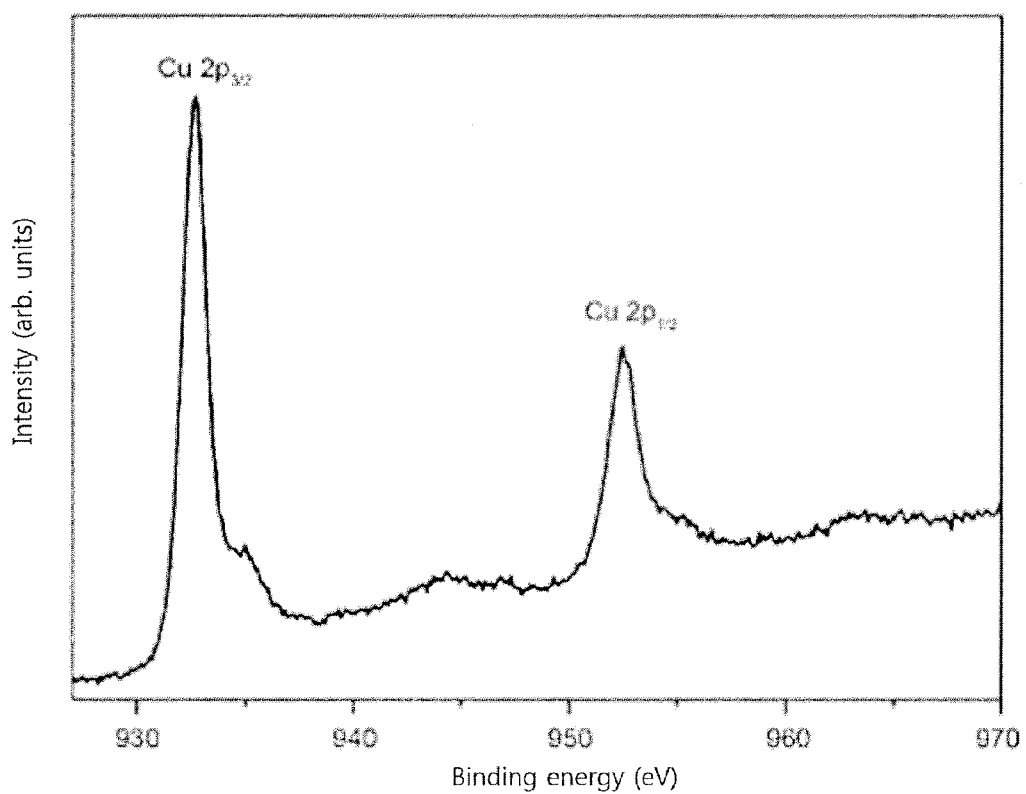
FIG. 4 shows the XPS spectrum of copper nanoparticles according to an embodiment of the present invention.

FIG. 4 shows the XPS spectrum of copper nanoparticles according to an embodiment of the present invention. Referring to FIG. 4, the copper nanoparticles showed two main peaks at 932.8 and 953.7 eV corresponding to binding energy values of Cu $2p_{3/2}$ and Cu $2p_{1/2}$, respectively. The difference in binding energy between Cu and $Cu_2O$ is very low (0.1-0.2 eV). Therefore, it is considered that it is very difficult to accurately measure the difference between Cu and $Cu_2O$ by XRD analysis.

Meanwhile, the BET surface area of the copper nanoparticles immobilized on activated carbon was measured to be 654.0 $m^2g^{-1}$. To measure the pore volume and pore size of the nanoparticles using the desorption branch of the isotherm, the Barrett-Joyner-Halenda (BJH) equation was used. As a result, the pore volume was measured to be 0.268 $cm^3g^{-1}$, and the pore size was measured to be 3.9 nm.

Figure 5:
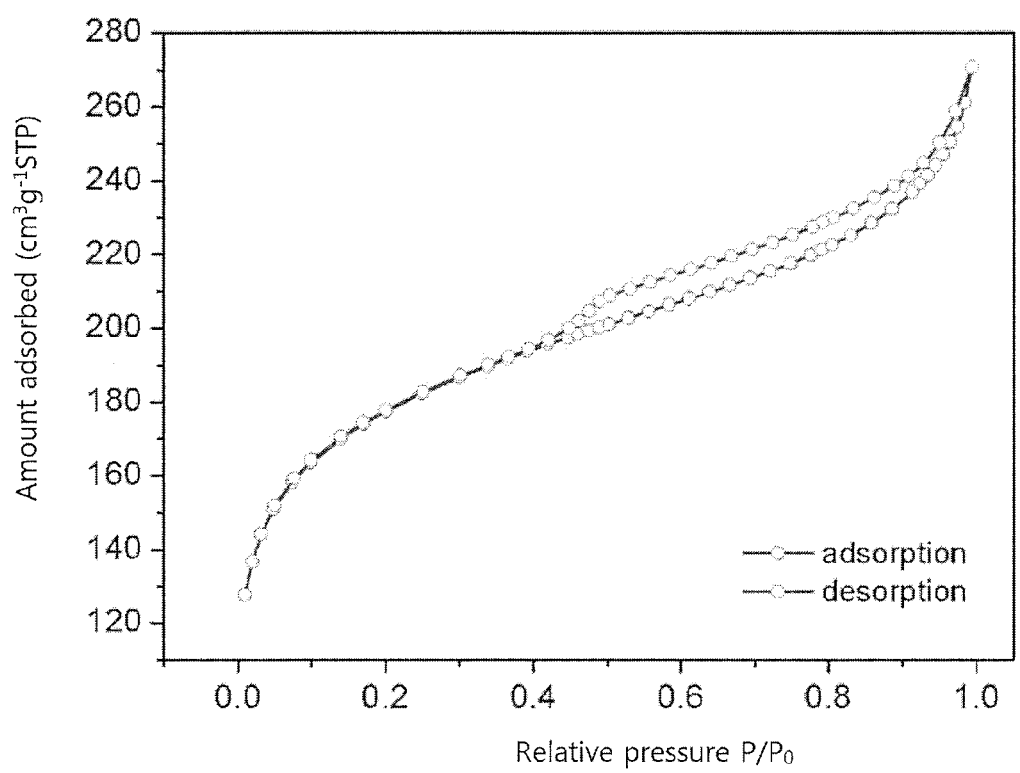
FIG. 5 is an $N_2$-adsorption isotherm graph of copper nanoparticles immobilized on activated carbon according to an embodiment of the present invention.

FIG. 5 is an $N_2$-adsorption isotherm graph of copper nanoparticles adsorbed on activated carbon according to an embodiment of the present invention. Referring to FIG. 5, it can be seen that the copper nanoparticles according to the present invention had mesopores. In other words, the copper nanoparticles on activated carbon displayed a Langmuir type IV isotherm corresponding to mesoporous materials having high surface areas. The copper nanoparticles on activated carbon showed high catalytic activity, a high surface area, enhanced dispersibility, and a sufficient ability to adsorb reactants, indicating that the copper nanoparticles have improved catalytic performance.

Next, the heterogeneity of the copper nanoparticles imobilized on activated carbon was measured by hot filtration and ICP analysis. For high filtration, a reaction between diphenyl diselenide and 2-formylphenylboronic acid was selected. The amount of copper eluted into the hot filter was about 0.0005% as measured by inductively coupled plasma atomic emission spectroscopy. The reaction was stopped at a conversion rate of 43%, followed by filtration. The reaction mixture was divided into two parts. The two divided parts were allowed to react at the same temperature of 100° C. for additional 6 hours. The part containing the copper nanoparticles showed a conversion rate of 99% (GC-MS). However, the part containing no catalyst showed a conversion rate of only 49% from the original conversion rate of 43%. Accordingly, it can be seen that catalytic reactions according to the present invention are mostly heterogeneous reactions.

To examine the need and role of copper in promoting a cross-coupling reaction, dibenzyl diselenide and copper nanoparticles immobilized on an excessive amount of activated carbon were reacted under the same reaction conditions without using phenylboronic acid. During the reaction, the solid intermediate $[(PhCH_2Se)_2-Cu)]$ was precipitated and centrifuged with ethanol several times. After centrifugation, the GC-MS analysis of the combined supernatants indicated that the starting material dibenzyl diselenide completely disappeared.

Figure 6:
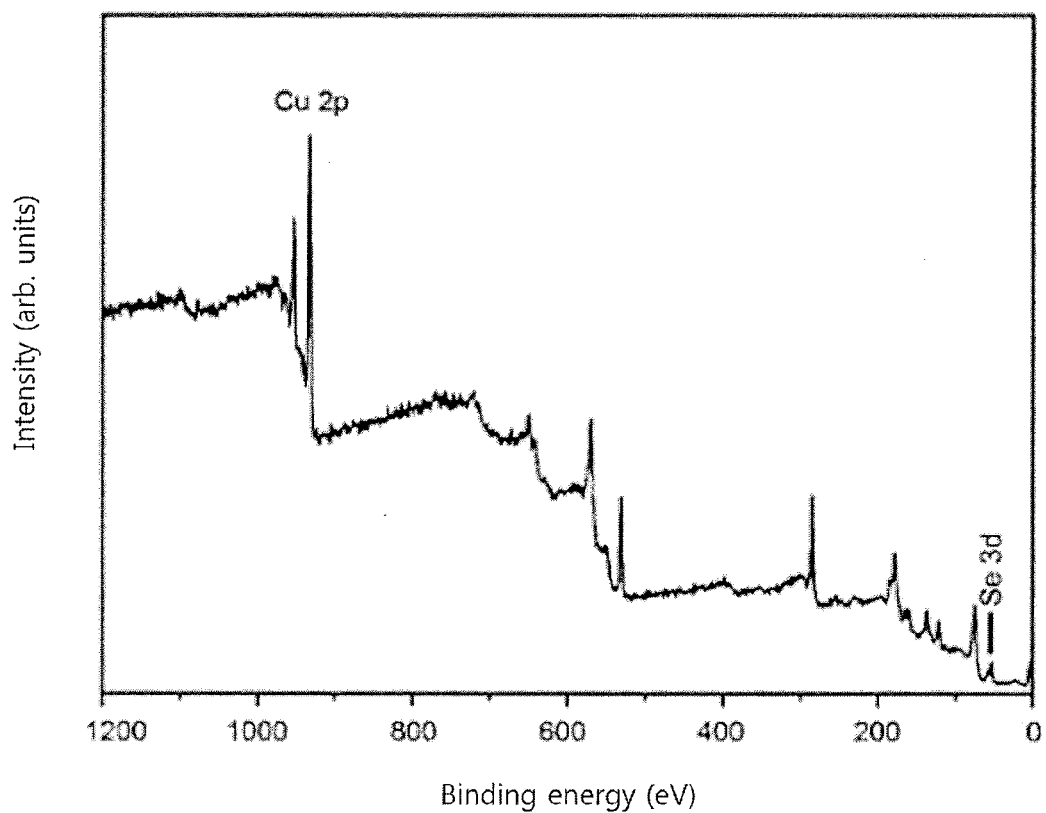
FIG. 6 shows the XPS spectrum of $[(PhCH_2Se)_2\text{-}Cu)]$ which is an intermediate of copper nanoparticles according to the present invention.

FIG. 6 shows the XPS spectrum of $[(PhCH_2Se)_2-Cu)]$ which is a solid intermediate of copper nanoparticles according to the present invention. As shown in FIG. 6, the XPS analysis of the intermediate indicates that a bond between copper (932.7 and 952.7 eV) and selenium (53.6 eV) is present. Since the intermediate is insoluble in all solvents, it is impossible to further identify a solid intermediate separated from unreacted copper nanoparticles.

Figure 7:
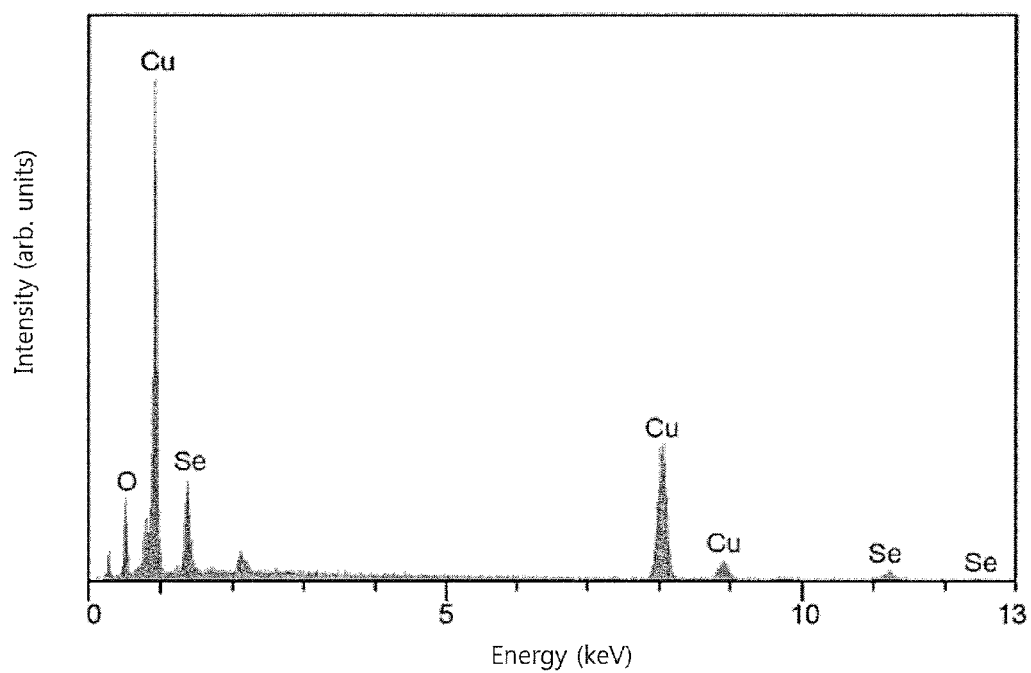
FIG. 7 shows the EDS spectrum of $[(PhCH_2Se)_2\text{-}Cu)]$ which is an intermediate of copper nanoparticles according to the present invention.

FIG. 7 shows the EDS spectrum of $[(PhCH_2Se)_2-Cu)]$ which is a solid intermediate of copper nanoparticles according to the present invention. Referring to FIG. 7, the EDS analysis further indicates that an intermediate containing a copper-selenium bond is present.

An additional reaction between the solid intermediate $[(PhCH_2Se)_2-Cu)]$ and phenylboronic acid in a DMSO solvent produced the cross-coupled product benzyl phenyl selenide in a yield of only 30% as shown in the following scheme:

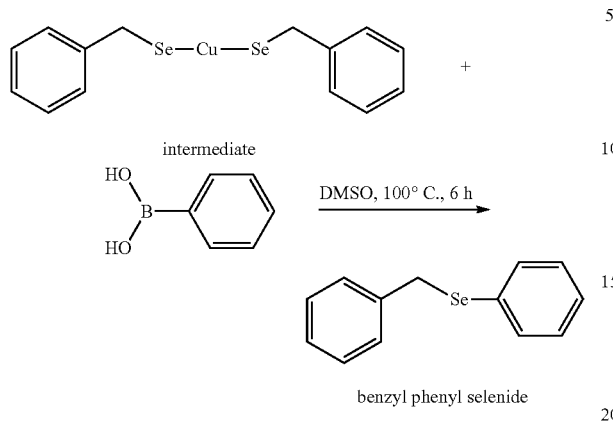

benzyl phenyl selenide

The same observation on sulfide was reported in N. Taniguchi, *J. Org. Chem.* 2007, 72, 1241-1245, which is a prior art document. According to this prior art document, it was reported that this low yield is attributable to insufficient oxidation or low solubility, and can be somewhat increased by the use of an additive.

The copper nanoparticles immnobilized on activated carbon, synthesized in Example 1, were used as a heterogeneous catalyst in a cross-coupling reaction between diphenyl diselenide and phenylboronic acid.

Example 2

Cross-Coupling Reaction Between Diphenyl Diselenide and Phenylboronic Acid

In this Example, various experiments were performed in order to optimize reaction conditions for a cross-coupling reaction between diphenyl diselenide and phenylboronic acid, and the results of the experiments are shown in Table 1 below.

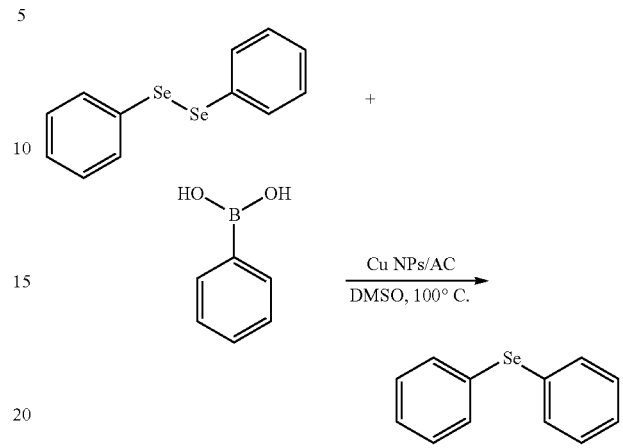

Diphenyl diselenide (0.32 nmol, 100 mg), phenylboronic acid (0.71 nmol, 86 mg), the copper nanoparticles (4 mole % based on diphenyl diselenide) prepared in Example 1, and a DMSO solvent (1 mL) were added to a 10 mL aluminum-capped vial. The mixture was sonicated at room temperature for 5 minutes, and then magnetically stirred in an oil bath preheated to 100° C.

The reaction was monitored by TLC. The reaction solution was cooled to room temperature, after which it was purified with diethyl ether and filtered through a celite bed. The filtrate was washed with water and a KOH solution to remove an excess of phenylboronic acid. The remaining solution was extracted with ether and, if required, washed with bromine water. The combined ether layers were dried with anhydrous magnesium sulfate, filtered, evaporated using a rotary evaporator, and then dried under a high vacuum. The crude product was analyzed by GC-MS.

TABLE 1

Optimization of cross-coupling reaction between diphenyl diselenide and phenylboronic acid using copper nanocatalyst immobilized on activated carbon

| Run No. | Solvent[b] | Catalyst [mol % Cu] | Temperature [° C.] | Yield[c] [%] |
|---|---|---|---|---|
| 1 | DMSO | — | 100 | 5 |
| 2 | DMSO | 4 | RT | 0 |
| 3 | DMSO | 4 | 80 | 32 |
| 4 | DMSO | 3 | 100 | 93 |
| 5 | DMSO | 4 | 100 | 100 |
| 6 | DMSO | 4 | 100 | trace amount[d] |
| 7 | DMF | 4 | 100 | 97 |
| 8 | DMA | 4 | 100 | 91 |
| 9 | NMP | 4 | 100 | 89 |
| 10 | DMPU | 4 | 100 | 95 |
| 11 | dioxane | 4 | reflux | 15 |
| 12 | [BMIM][BF4] | 4 | 100 | 8 |
| 13 | glycerol | 4 | 100 | 3 |
| 14 | PEG | 4 | 100 | 13 |
| 15 | EG | 4 | 100 | 7 |
| 16 | DMC | 4 | reflux | 0 |

TABLE 1-continued

Optimization of cross-coupling reaction between diphenyl diselenide and
phenylboronic acid using copper nanocatalyst immobilized on activated carbon

[Reaction scheme: diphenyl diselenide + phenylboronic acid (HO)₂B-Ph → diphenyl selenide, with Cu NPs/AC, DMSO, 100° C., Time]

| Run No. | Solvent[b] | Catalyst [mol % Cu] | Temperature [° C.] | Yield[c] [%] |
|---|---|---|---|---|
| 17 | toluene | 4 | 100 | 0 |
| 18 | DMSO | recovered from No. 5 | 100 | 100 |
| 19 | DMSO | recovered from No. 18 | 100 | 100 |
| 20 | DMSO | recovered from No. 19 | 100 | 89 |
| 21 | DMSO | recovered from No. 20 | 100 | 80 |
| 22 | DMSO | recovered from No. 21 | 100 | 73 |

[a]Reaction conditions: diphenyl diselenide (0.64 mmol); phenylboronic acid (1.41 mmol); amount of copper nanoparticle catalyst based on diphenyl diselenide = 4 mole %; reaction temperature = 100° C.; reaction time = 3 hr;
[b]1 mL solvent;
[c]yield measured by GC-MS analysis;
[d]reaction under $N_2$ atmosphere Referring to run No. 1 in Table 1 above, it can be seen that the reaction performed without the catalyst showed a yield of only 5%. Referring to run No. 2, it can be seen that, when the reaction was performed in the presence of 4 mole % of the catalyst at room temperature for 12 hours, no coupled product was synthesized.

Meanwhile, experimental conditions were screened at a constant catalyst concentration of 4 mole %. In run No. 3, a yield of 32% was obtained by increasing the reaction temperature from room temperature to 80° C. while maintaining the reaction temperature at 3 hours. However, in run No. 4, a decrease in the amount of the catalyst led to a decrease in the yield. In run No. 5, the highest yield, that is, the reaction in which the reactant diphenyl diselenide completely disappeared without any byproduct as confirmed by analysis, was obtained when the amount of the catalyst based on diphenyl diselenide in the DMSO solvent was 4 mole % and when the reaction was performed at a temperature of 100° C. for 3 hours. Referring to run No. 6, a trace amount of the product was obtained when the same experiment was performed in DMSO while bubbling nitrogen gas. Accordingly, it can be seen that air is essential in the cross-coupling reaction according to the present invention.

Referring to run Nos. 7 to 10, other solvent systems, including N,N'-dimethylformamide (DMF), N,N'-dimethylacetamide (DMA), N-methyl pyrrolidinone (NMP) and N,N'-dimethylpropylene urea (DMPU), also showed satisfactory results. Referring to run Nos. 11 to 17, solvents, such as dioxane, 1-butyl-3-methylimidazolium tetrafluoroborate ([BMIM][BF₄]) ionic liquid, glycerol, polyethylene glycol (PEG), ethylene glycol (EG), dimethyl carbonate (EMC) and toluene, reduced the yield of the product.

Thereafter, the recyclability of the catalyst used in the cross-coupling reaction between diphenyl diselenide and phenylboronic acid under optimized conditions was evaluated. The reaction temperature was 100° C., and the copper nanoparticles were used in an amount of 4 mole %.

Figure 8:
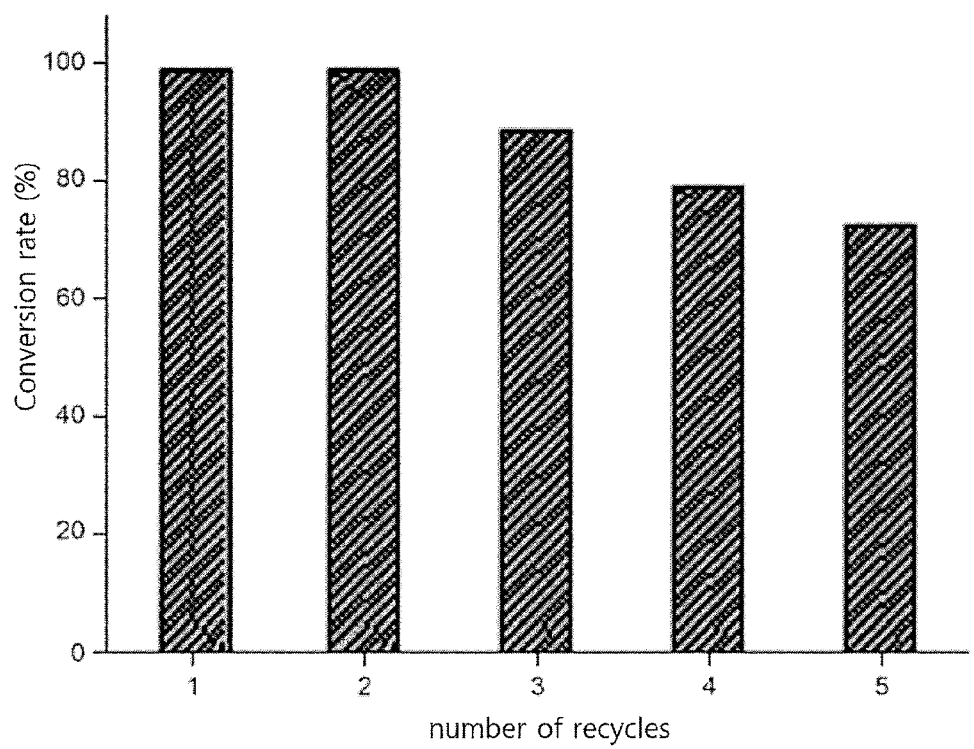
FIG. 8 is a graph showing conversion rate as a function of the number of recycles of copper nanoparticles used in a cross-coupling reaction between diphenyl selenide and phenylboronic acid according to an embodiment of the present invention.

FIG. 8 is a graph showing conversion rate as a function of the number of recycles of copper nanoparticles used in a cross-coupling reaction between diphenyl selenide and phenyl boronic acid according to an embodiment of the present invention. Referring to FIG. 8 and run Nos. 18 and 19 in Table 1 above, the first two recycles of the reaction showed a perfect conversion rate. Referring to run Nos. 20 to 22, it can be seen that the activity of the catalyst in subsequent sequential reactions slightly decreased. The decrease in the activity of the catalyst is attributable to the oxidation of the copper nanoparticles in air, and is unavoidable in the reaction because air acts as an oxidizing agent in the reaction. It should be noted that the reaction in the presence of nitrogen gas produced a trace amount of the coupled product.

Figure 9:
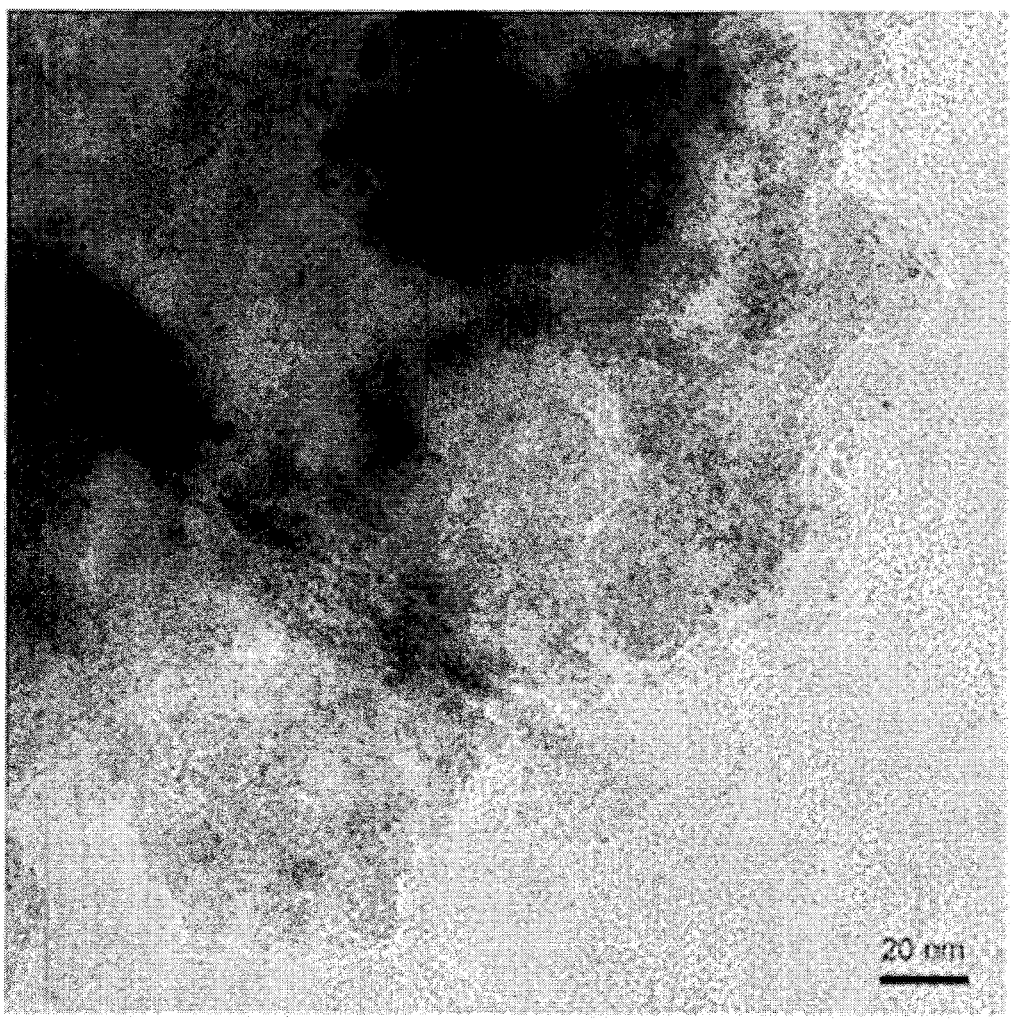
FIG. 9 is a TEM image of copper nanoparticles recycled three times according to an embodiment of the present invention.

FIG. 9 is a TEM image of copper nanoparticles recycled three times according to an embodiment of the present invention. As shown in FIG. 9, the copper nanoparticles strongly aggregated at high reaction temperature. Since the copper nanoparticles aggregate into larger colloids, the activity of the catalyst decreases.

Comparative Example 1

Coupling Reaction Between Diphenyl Diselenide and Phenylboronic Acid Using Conventional Copper Catalyst Cross-coupling reactions between diphenyl diselenide and phenylboronic acid were performed using a conventional copper catalyst as a heterogeneous catalyst under the conditions as described in Example 1, and the results of the reactions are shown in Table 2 below:

TABLE 2

| Run No. | Solvent | Catalyst [mol % Cu] | Temperature [° C.] | Yield (%) |
|---|---|---|---|---|
| 1 | DMSO | CuO hollow spheres | 100 | 84 |
| 2 | DMSO | $Cu_2O$ cubes | 100 | 89 |
| 3 | DMSO | Cu nanoparticles | 100 | 74 |

In order to demonstrate the advantages of the copper nanoparticles immobilized on activated carbon according to the present invention, reactions were performed using different homogeneous catalysts (containing 4 mole % of copper). Run No. 1 in Table 2 above is a reaction performed using CuO hollow spheres (see, for example, M. Bonaterra, S. E. Martin, and R. A. Rossi, *Tetrahedron Lett.* 2006, 47, 3511-3515) as a catalyst; run No. 2 is a reaction performed using $Cu_2O$ cubes (see, for example, J. H. Cheng, C. L. Yi, T. J. Liu, and C. F. Lee, Chem. Commun. 2012, 48, 8440-8442) as a catalyst; and run No. 3 is a reaction using copper nanoparticles (see, for example, J. M. Becht, and C. L. Drian, J. Org. Chem. 2011, 76, 6327-6330) as a catalyst. Referring to FIG. 2, it can be seen that the reactions were also easily performed, but showed low yields compared to reactions performed under the same conditions using as a catalyst the copper nanoparticles synthesized from $[Cu_3(BTC)_2]$ according to the present invention. In conclusion, it can be seen that the copper nanoparticles according to the present invention exhibit high catalytic activity and excellent recyclability compared to conventional CuO hollow spheres including divalent copper nanoparticles, conventional $Cu_2O$ nanocubes comprising monovalent nanoparticles, and conventional copper nanoparticles.

Example 3

Cross-Coupling Reactions Between Diphenyl Diselenide and Various Boronic Acids Using Copper Nanoparticles Immobilized on Activated Carbon as Catalyst In order to examine whether the catalyst system according to the present invention can also be applied to materials having various substituents, cross-coupling reactions between diphenyl diselenide and arylboronic acids substituted with various substituents were performed, and the results of the reactions are shown in Table 3 below. Cross-coupling reactions between diphenyl dichalcogenide and boronic acids were performed only in the presence of a solid copper nanoparticle catalyst, and there was no precipitation by copper atoms dissolved in the reaction solution.

TABLE 3

Cross-coupling reactions[a] between diphenyl diselenide and various boronic acids using copper nanoparticles immobilized on activated carbon as catalyst

| Run No. | Boronic acid | Product | Time [h] | Yield [%][b] |
|---|---|---|---|---|
| 1 | 4-methoxyphenylboronic acid | phenyl(4-methoxyphenyl)selenide | 3 | 100 |
| 2 | 4-methylphenylboronic acid | phenyl(4-methylphenyl)selenide | 4 | 100 |
| 3 | 2,4,6-trimethylphenylboronic acid | phenyl(2,4,6-trimethylphenyl)selenide | 6 | 97 |
| 4 | 2,6-dimethoxyphenylboronic acid | phenyl(2,6-dimethoxyphenyl)selenide | 6 | 61 |
| 5 | 2-naphthylboronic acid | phenyl(2-naphthyl)selenide | 5 | 100 |

TABLE 3-continued

Cross-coupling reactions[a] between diphenyl diselenide and
various boronic acids using copper nanoparticles immobilized on activated carbon as catalyst

| Run No. | Boronic acid | Product | Time [h] | Yield [%][b] |
|---|---|---|---|---|
| 6 | 4-acetylphenylboronic acid, B(OH)$_2$ with para COCH$_3$ | phenyl 4-acetylphenyl selenide | 6 | 94 |
| 7 | 4-(ethoxycarbonyl)phenylboronic acid, B(OH)$_2$ with para COOC$_2$H$_5$ | ethyl 4-(phenylselanyl)benzoate | 6 | 99 |
| 8 | 4-(trifluoromethyl)phenylboronic acid, B(OH)$_2$ with para CF$_3$ | phenyl 4-(trifluoromethyl)phenyl selenide | 6 | 100 |
| 9 | 4-cyanophenylboronic acid, B(OH)$_2$ with para CN | 4-(phenylselanyl)benzonitrile | 6 | 96 |
| 10 | 4-biphenylboronic acid, (HO$_2$)B–biphenyl | 4-(phenylselanyl)biphenyl | 6 | 99 |
| 11 | 2-formylphenylboronic acid, B(OH)$_2$ with ortho CHO | 2-(phenylselanyl)benzaldehyde | 9 | 100 |

TABLE 3-continued

Cross-coupling reactions[a] between diphenyl diselenide and various boronic acids using copper nanoparticles immobilized on activated carbon as catalyst

| Run No. | Boronic acid | Product | Time [h] | Yield [%][b] |
|---|---|---|---|---|
| 12 | 4-F-C6H4-B(OH)2 | PhSe-C6H4-F | 6 | 95 |
| 13 | 4-Br-C6H4-B(OH)2 | PhSe-C6H4-Br | 4 | 100 |
| 14 | 3-pyridyl-B(OH)2 | PhSe-(3-pyridyl) | 6 | 99 |
| 15 | 3-thienyl-B(OH)2 | PhSe-(3-thienyl) | 6 | 100 |
| 16 | trans-PhCH=CH-B(OH)2 | PhSe-CH=CH-Ph | 6 | 100(99:1)[d] |
| 17 | PhC≡C-Bpin | PhSe-C≡C-Ph | 6 | 99 |

[a]Reaction conditions: diphenyl diselenide (0.64 mmol); substituted phenylboronic acid (2.2 equivalents); catalyst (4 mole % Cu); DMSO = 1 mL; 100° C.;
[b]yield was calculated as the average of two independent reactions by GC-MS;
[c]trans-2-phenylvinylboronic acid, Aldrich, No. 473790;
[d]selectivity by GC-MS = [E:Z, 99:1];
[e]2-phenyl-1-ethynylboronic acid pinacol ester, Aldrich, No. 686308

Referring to run Nos. 1 to 3 in Table 3 above, the products obtained from methoxyphenylboronic acid, methylphenylboronic acid and 2,4,6-trimethylphenylboronic acid, which are electron-donor groups, showed yields of 100%, 100% and 97%, respectively. However, referring to run No. 4, 2,6-dimethoxyphenylboronic acid showed moderate yield.

In addition, phenylboronic acids, which contain strong electron-withdrawing groups such as naphthyl, and 4-acetyl, 4-ethoxycarbonyl, 4-trifluoromethyl, 4-cyano, 4-biphenyl and even 2-formyl groups, were very tolerant to the catalyst system of the present invention. Meanwhile, referring to run Nos. 12 and 13, it can be seen that, in the case of a phenylboronic acid containing halogen, the coupling reaction proceeded mildly to produce the corresponding aryl phenyl selenide product.

A phenylboronic acid that may be used in the present invention may be represented by the following formula 1, but is not limited thereto:

Formula 1

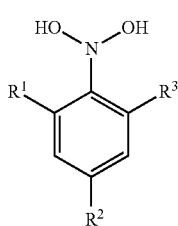

where $R^1$, $R^2$ and $R^3$ are the same or different and are selected from the group consisting of hydrogen, a $C_1$-$C_3$ alkyl group, a $C_1$-$C_3$ alkoxy group, an acetyl group, an ethoxycarbonyl group, a trifluoromethyl group, a cyano group, a biphenyl group, a formyl group, and a halogen group.

Referring to run Nos. 14 and 15 in Table 3, the heterocyclic boronic acids also produced the corresponding cross-coupling reaction products in high yields. Referring to run Nos. 16 and 17, the catalyst system according to the present invention was well compatible with trans-2-phenylvinylboronic acid and 2-phenyl-1-ethynylboronic acid pinacol ester, and produced (E) and (Z)-(styryl) (phenyl) selenide (E/Z, 99:1) and phenyl(phenylethynyl) selane in yields of 99% and 100%, respectively.

In conclusion, when the reactions were performed in a DMSO solvent at a temperature of 100° C. in the presence of 4 mole % of the catalyst, all the boronic acids used could produce products in high yields.

Example 4

Evaluation of Catalyst in Reaction Between Dibenzyl Selenide and Substituted Boronic Acid or Ester Using Copper Nanoparticles Immobilized on Activated Carbon as Catalyst Thereafter, cross-coupling reactions were performed using dibenzyl diselenide as a reaction substrate under the optimized conditions, and the results of the reaction are shown in Table 4 below:

TABLE 4

Evaluation of catalyst in reaction between dibenzyl selenide and substituted boronic acid or ester using copper nanoparticles immobilized on activated carbon as catalyst[a]

| Run No. | Boronic acid | Product | Time [h] | Yield [%] |
|---|---|---|---|---|
| 1 | 4-methoxyphenyl-B(OH)$_2$ | benzyl-Se-(4-OCH$_3$-phenyl) | 5 | 94 |
| 2 | (HO)$_2$B-CH=CH-phenyl | benzyl-Se-CH=CH-phenyl | 5 | 100(100)[b] |
| 3 | pinacol ester of phenylethynyl-boronate | benzyl-Se-C≡C-phenyl | 6 | 100 |

[a]The same reaction conditions as described in Example 3;
[b]selectivity by GC-MS: [100% E-isomer]

Referring to Table 4 above, the reactions were performed in a DMSO solvent at room temperature for 5-6 hours using the catalyst in an amount of 4 mole % based on dibenzyl diselenide, cross-coupling products having Se-sp$^3$, Se-sp$^2$ and Se-sp bonds, respectively, were obtained. Referring to run Nos. 2 and 3, the reactions of trans-2-phenylvinylboronic acid and 2-phenyl-1-ethynylboronic acid pinacol ester also showed good yields under the same conditions as described in Example 3.

Example 5

Examination of Applicability of Catalyst to Diphenyl Ditelluride

The catalyst system according to the present invention was used in reactions for synthesizing various ditelluride derivatives, and the results of the reactions are shown in Table 5 below.

TABLE 5

Examination of applicability of catalyst to diphenyl ditelluride[a]

| Run No. | Boronic acid | Product | Time [h] | Yield [%] |
|---|---|---|---|---|
| 1 | 2-formylphenylboronic acid B(OH)$_2$ | phenyl(2-formylphenyl) tellane | 18 | 100 |
| 2 | trans-2-phenylvinylboronic acid (HO)$_2$B | | 18 | 100(100)[b] |
| 3 | 2-phenyl-1-ethynylboronic acid pinacol ester | | 18 | 30, 100[c] |

[a] Reaction conditions: diphenyl ditelluride (0.48 mmol); substituted boronic acid or ester (2.2 eq); catalyst (4 mole % Cu) for diphenyl ditelluride; DMSO = 1 mL; room temperature; 18 hours;
[b] selectivity: [100% E-isomer];
[c] reaction at 100° C. for 6 hours More specifically, the activity of the catalyst was evaluated in reactions between diphenyl ditelluride and 2-formylphenylboronic acids that were sterically hindered compounds having an electron-withdrawing group. The reactions were performed at room temperature for 18 hours. Referring to run No. 1 in Table 5 above, it can be seen that the reactants were completely converted to phenyl(2-formylphenyl) tellane without any adduct. Referring to run No. 2, it can be seen that trans-2-phenylboronic acid that was an alternative coupling reaction compound also showed perfect selectivity at room temperature and produced the corresponding produce in high yield. Referring to run No. 3, when 2-phenyl-1-ethynylboronic acid pinacol ester was reacted at room temperature, the yield was reduced to 30%. However, it can be seen that, when the reaction was performed at 100° C. for 6 hours, the yield increased to 100%. According to Example 5, organotellurium derivatives can be synthesized from boronic acid at room temperature without using any additive.

According to the present invention, copper nanoparticles having high catalytic activity can be synthesized from [Cu$_3$(BTC)$_2$] and NaBH$_4$ via a simple chemical reduction method. The prepared copper nanoparticles can be used as an effective heterogeneous catalyst for a cross-coupling reaction between diphenyl dichalcogenide and boronic acid to produce a multipurpose metal-carbon bond without having to use any additive. This catalyst system shows excellent reactivity in various reactions with Se- and Te-carbon bonds, such as Se-aryl, Se-vinyl, Se-alkynyl, Te-aryl, Te-vinyl and Te-alkynyl bonds, even when it is used in a small amount without ligand and other additives. The copper nanoparticle catalyst system according to the present invention is a heterogeneous catalyst system which is very advantageous in terms of atom economy, and can be recycled without reducing the activity thereof.

As described above, according to the present invention, Cu/Cu$_2$O core-shell copper nanoparticles having high catalytic activity can be synthesized from [Cu$_3$(BTC)$_2$] and NaBH$_4$ via a simple chemical reduction method. The prepared copper nanoparticles are simple and inexpensive, have a large surface area, and thus act as an efficient heterogeneous catalyst in the synthesis of organochalcogen derivatives. Accordingly, these copper nanoparticles can be used as an effective heterogeneous catalyst for cross-coupling reactions between diphenyl dichalcogenide and various boronic acids to produce a multipurpose metal-carbon bond. Such cross-coupling reactions are performed via a simple process, and the nanoparticle catalyst according to the present invention is compatible with various substrates under mild reaction conditions and shows excellent recyclability while the catalytic activity thereof is not reduced.

Although the present invention has been described in detail in conjunction with the specific embodiments, it will be apparent to those skilled in the art that various modifications and alterations are possible without departing from the spirit and scope of the invention, and thus all these modifications and alterations should be construed to fall within the range of protection of the present invention.

What is claimed is:

1. A method of preparing immobilized copper nanoparticles, the method comprising:

adding $Cu(NO_3)_2 \cdot 2.5H_2O$ and $H_3BTC$ to an organic solvent, followed by stirring to prepare a mixture;

separating a solid product from the mixture, and drying the separated product in a vacuum to yield $[Cu_3(BTC)_2]$;

adding an aqueous solution of $NaBH_4$ dropwise to an aqueous solution of the $[Cu_3(BTC)_2]$ in water to obtain reduced copper particles;

adding the reduced copper particles to a mixture of ethyl alcohol and activated carbon, followed by sonication at room temperature and refluxing to obtain a solution of copper nanoparticles immobilized on the activated carbon; and cooling the solution of the copper nanoparticles immobilized on the activated carbon, and purifying a product resulting from the cooling of the solution.

2. The method of claim 1, wherein the copper nanoparticles have a $Cu/Cu_2O$ core-shell structure with a core composed of zero-valent copper and a shell composed of monovalent copper.

3. The method of claim 1, wherein the organic solvent is a mixed solvent obtained by mixing dimethylformamide, ethanol and water at a ratio of 1:1:1.

4. A method of preparing a chalcogenide compound the method comprising:

adding $Cu(NO)_2 \cdot 2.5H_2O$ and HBTC to an organic solvent, followed by stirring to prepare a mixture;

separating a solid product from the mixture, and drying the separated product in a vacuum to yield $[Cu_3(BTC)_2]$;

adding an aqueous solution of $NaBH_4$ dropwise to an aqueous solution of the $[Cu_3(BTC)]$ in water to obtain reduced copper particles;

adding the reduced copper particles to a mixture of ethyl alcohol and activated carbon, followed by sonication at room temperature and refluxing to obtain a solution of copper nanoparticles immobilized on the activated carbon;

obtaining an immobilized copper nanoparticles by cooling the solution of the copper nanoparticles immobilized on the activated carbon, and purifying a product resulting from the cooling of the solution; and performing a cross-coupling reaction between diphenyl dichalcogenide and phenylboronic acid in the presence of the immobilized copper nanoparticles as a catalyst.

5. A method of preparing a chalcogenide compound, the method comprising:

adding $Cu(NO_3)_2 \cdot 2.5H_2O$ and $H_3BTC$ to an organic solvent, followed by stirring to prepare a mixture;

separating a solid product from the mixture, and drying the separated product in a vacuum to yield $[Cu_3(BTC)_2]$;

adding an aqueous solution of $NaBH_4$ dropwise to an aqueous solution of the $[Cu_3(BTC)_2]$ in water to obtain reduced copper particles;

adding the reduced copper particles to a mixture of ethyl alcohol and activated carbon, followed by sonication at room temperature and refluxing to obtain a solution of copper nanoparticles immobilized on the activated carbon;

obtaining an immobilized copper nanoparticles by cooling the solution of the copper nanoparticles immobilized on the activated carbon, and purifying a product resulting from the cooling of the solution; and performing a cross-coupling reaction between dibenzyl dichalcogenide and phenylboronic acid in the presence of the immobilized copper nanoparticles as a catalyst.

6. The method of claim 4, wherein the cross-coupling reaction comprises:

mixing diphenyl dichalcogenide or dibenzyl dichalcogenide with phenylboronic acid in an organic solvent to obtain a reaction solution, and sonicating the reaction solution at room temperature;

magnetically stirring the reaction solution in an oil bath preheated to 100° C.; and purifying and drying a product resulting from the magnetic stirring.

7. The method of claim 4, wherein the diphenyl dichalcogenide is diphenyl diselenide or diphenyl ditelluride.

8. The method of claim 5, wherein the dibenzyl dichalcogenide is diphenyl diselenide or diphenyl ditelluride.

9. The method of claim 4, wherein the phenylboronic acid is represented by the following formula 1:

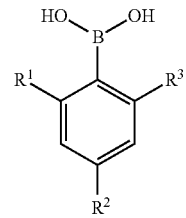

Formula 1 where $R^1$, $R^2$ and $R^3$ are identical or different and are selected from the group consisting of hydrogen, a $C_1$-$C_3$ alkyl group, a $C_1$-$C_3$ alkoxy group, an acetyl group, an ethoxycarbonyl group, a trifluoromethyl group, a cyano group, a biphenyl group, a formyl group, and a halogen group.

10. The method of claim 6, wherein the organic solvent is at least one selected from the group consisting of dimethyl sulfoxide (DMSO), N,N'-dimethylformamide (DMF), N,N'-dimethylacetamide (DMA), N-methyl pyrrolidinone (NMP), and N,N'-dimethylpropylene urea (DMPU).

11. The method of claim 4, wherein the cross-coupling reaction is performed using the catalyst in an amount of 4 mole % based on diphenyl diselenide, in DMSO as a solvent at a temperature of 100° C. for 3-9 hours.

12. The method of claim 7, wherein the diphenyl dichalcogenide is diphenyl ditelluride, and the cross-coupling reaction is performed at room temperature.

13. A method of preparing a dichalcogenide compound the method comprising:
adding $Cu(NO_3)_2 \cdot 2.5H_2O$ and $H_1BTC$ to an organic solvent, followed by stirring to prepare a mixture;
separating a solid product from the mixture, and drying the separated product in a vacuum to yield $[Cu_3(BTC)_2]$;
adding an aqueous solution of $NaBH_4$ dropwise to an aqueous solution of the $[Cu_3(BTC)_2]$ in water to obtain reduced copper particles;
adding the reduced copper particles to a mixture of ethyl alcohol and activated carbon, followed by sonication at room temperature and refluxing to obtain a solution of copper nanoparticles immobilized on the activated carbon;
obtaining an immobilized copper nanoparticles by cooling the solution of the copper nanoparticles immobilized on the activated carbon, and purifying product resulting from the cooling of the solution; and
performing a cross-coupling reaction between diphenyl dichalcogenide and heterocyclic aromatic boronic acid in the presence of the immobilized copper nanoparticles as a catalyst.

14. A method of preparing a dichalcogenide compound the method comprising:
adding $Cu(NO_3)_2 \cdot 2.5H_2O$ and HBTC to an organic solvent, followed by stirring to prepare a mixture;
separating a solid product from the mixture, and drying the separated product in a vacuum to yield $[Cu_3(BTC)_2]$;
adding an aqueous solution of $NaBH_4$ dropwise to an aqueous solution of the $[Cu_3(BTC)_2]$ in water to obtain reduced copper particles;
adding the reduced copper particles to a mixture of ethyl alcohol and activated carbon, followed by sonication at room temperature and refluxing to obtain a solution of copper nanoparticles immobilized on the activated carbon;
obtaining an immobilized copper nanoparticles by cooling the solution of the copper nanoparticles immobilized on the activated carbon, and purifying a product resulting from the cooling of the solution; and
performing a cross-coupling reaction between dibenzyl dichalcogenide and heterocyclic aromatic boronic acid in the presence of the immobilized copper nanoparticles as a catalyst.

15. The method of claim 13, wherein the heterocyclic aromatic boronic acid has a nitrogen or sulfur substituent in at least one CH unit in an aromatic ring thereof.

16. A method of preparing styryl phenyl selenide, the method comprising:
adding $Cu(NO_3)_2 \cdot 2.5H_2O$ and $H_3BTC$ to an organic solvent, followed by stirring to prepare a mixture;
separating a solid product from the mixture, and drying the separated product in a vacuum to yield $[Cu_3(BTC)_2]$;
adding an aqueous solution of $NaBH_4$ dropwise to an aqueous solution of the $[Cu_3(BTC)_2]$ in water to obtain reduced copper particles;
adding the reduced copper particles to a mixture of ethyl alcohol and activated carbon, followed by sonication at room temperature and refluxing to obtain a solution of copper nanoparticles immobilized on the activated carbon;
obtaining an immobilized copper nanoparticles by cooling the solution of the copper nanoparticles immobilized on the activated carbon, and purifying a product resulting from the cooling of the solution; and
performing a cross-coupling reaction between diphenyl dichalcogenide and trans-2-phenylvinylboronic acid in the presence of the immobilized copper nanoparticles as a catalyst.

17. A method of preparing phenyl(phenylethynyl)selane, the method comprising:
adding $Cu(NO_3)_2 \cdot 2.5H_2O$ and HBTC to an organic solvent, followed by stirring to prepare a mixture;
separating a solid product from the mixture, and drying the separated product in a vacuum to yield $[Cu_3(BTC)_2]$;
adding an aqueous solution of $NaBH_4$ dropwise to an aqueous solution of the $[Cu_3(BTC)_2]$ in water to obtain reduced copper particles;
adding the reduced copper particles to a mixture of ethyl alcohol and activated carbon, followed by sonication at room temperature and refluxing to obtain a solution of copper nanoparticles immobilized on the activated carbon;
obtaining an immobilized copper nanoparticles by cooling the solution of the copper nanoparticles immobilized on the activated carbon, and purifying a product resulting from the cooling of the solution; and
performing a cross-coupling reaction between diphenyl dichalcogenide and 2-phenyl-1-ethynylboronic acid pinacol ester in the presence of the immobilized copper nanoparticles as a catalyst.

* * * * *